United States Patent [19]

Kikuchi et al.

[11] Patent Number: 5,043,446

[45] Date of Patent: Aug. 27, 1991

[54] PROCESS FOR THE PREPARATION OF PTERIN DERIVATIVES

[75] Inventors: Haruhiko Kikuchi, Saitama; Kenji Mori, Tokyo, both of Japan

[73] Assignee: Nisshin Flour Milling Co., Ltd., Tokyo, Japan

[21] Appl. No.: 485,274

[22] Filed: Feb. 23, 1990

[30] Foreign Application Priority Data

Feb. 28, 1989 [JP] Japan .................................. 1-45357

[51] Int. Cl.$^5$ ........................................ C07D 475/04
[52] U.S. Cl. .................................... 544/258; 536/121
[58] Field of Search ...................... 536/121; 544/258

[56] References Cited

U.S. PATENT DOCUMENTS 4,937,342 6/1990 Kurono et al. ...................... 544/258

FOREIGN PATENT DOCUMENTS 0079574 3/1983 European Pat. Off. ............ 544/258
221380 9/1989 Japan .
500999 2/1971 Switzerland .

OTHER PUBLICATIONS

Patterson et al., J. Am. Chem. Soc., 78, 5868 (1956).
Sugimoto and Matsuura, Bull. Chem. Soc. Jpn., 48, 3767 (1975).
Schircks and Bieri Viscontini et al., Helv. Chim. Acta., 60, 211 (1977).
Taylor et al., J. Am. Chem. Soc., 96, 6781 (1974).
Viscontini et al., Helv. Chim. Acta., 55, 574 (1972).
Chemistry of Organic Synthesis, 46, No. 6, 570 (1988).
Letti et al., Bull. Soc. Chim. Fr., 2299 (1972).
Snyder et al, Carbohydrate Research, 163, 169 (1987).
Kikuchi, S., Doctoral Dissertation, Tokyo Univ., Dec. 1989.
Mori et al., Liebigs Ann. Chem., 1989, 1267-9.
Kikuchi et al., Agric. Biol. Chem., vol. 53, No. 8, pp. 2095-2100 (1989).
Mori et al., Liebigs Ann. Chem., 1989, pp. 963-967.
Mori et al., Chem. Abstr., vol. 112, Entry 55447n.
Kikuchi et al., Chem. Abstr., vol. 112, Entry 55443h.
Jones et al., Jour. Carbohydr., Nucleosides, Nucleotides, vol. 6, No. 2, pp. 127-148 (1979).
Buchanan et al., Carbohydrate Res. vol. 36 (1974), pp. C5-C7.

*Primary Examiner*—Donald G. Daus
*Attorney, Agent, or Firm*—Abelman, Frayne & Schwab

[57] ABSTRACT

A process of preparing l-biopterin is disclosed which comprises the steps of:

Subjecting to selective Grignard reaction D-ribose having the hydroxyl groups in the 2- and 3-positions protected by an acetal group to give 6-deoxy-3,4-O-alkylidene allitol;

subjecting the 1- and 2-positions of said allitol to oxidative cleavage to form 5-deoxy-2,3-O-alkylidene-L-ribose followed by deacetalization to give 5-deoxy-L-ribose;

reacting 5-deoxy-L-ribose with a hydrazine compound to form a 5-deoxy-L-ribose hydrazone compound; and subjecting said hydrazone compound to condensation reaction with an acid addition salt of 4-hydroxy-2,5,6-triaminopyrimidine followed by oxidation.

6 Claims, No Drawings

PROCESS FOR THE PREPARATION OF PTERIN DERIVATIVES

FIELD OF THE INVENTION

This invention relates to new processes for the preparation of l-biopterin which is expected as a precursor of (6R)-tetrahydrobiopterin useful as a therapeutic agent for Perkinsons's disease and other diseases resulting from the disorder of nerve transmission system. The invention also relates to 6-deoxy-3,4-O-cyclohexylidene-L-allitol and 5deoxy-L-ribose phenylhydrazone which are new compounds produced as intermediates in the synthesis of l-biopterin from D-ribose.

BACKGROUND OF THE INVENTION

The prior art processes for the preparation of l-biopterin include:

(1) Reaction of 4-hydroxy-2,5,6-triaminopyrimidine (TAP) and 5-deoxy-L-arabinose in accordance with the following reaction formula

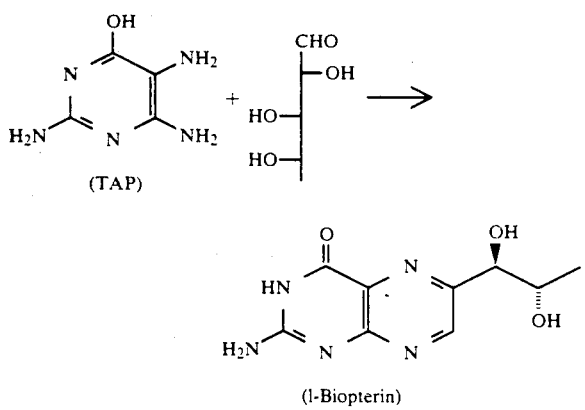

(E. L. Patterson et al., J. Am. Chem. Soc., 78, 5868 (1956)), (2) Reaction of TAP and 5-deoxy-L-arabinose phenylhydrazone in accordance with the following reaction formula

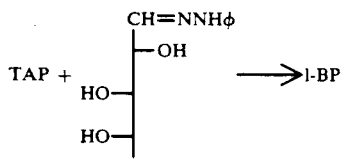

(Matsuura et al., Bull. Chem. Soc. Jpn., 48, 3767 (1975)), (3) Reaction of TAP and triacetyloxy-5-deoxy-L-arabinose phenylhydrazone in accordance with the following reaction formula

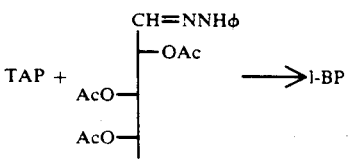

(M. Viscontini et al., Helv. Chim. Acta., 60, 211 (1977)), (4) Reaction of oxime and benzyl α-aminocyanoacetate in accordance with the following reaction formula

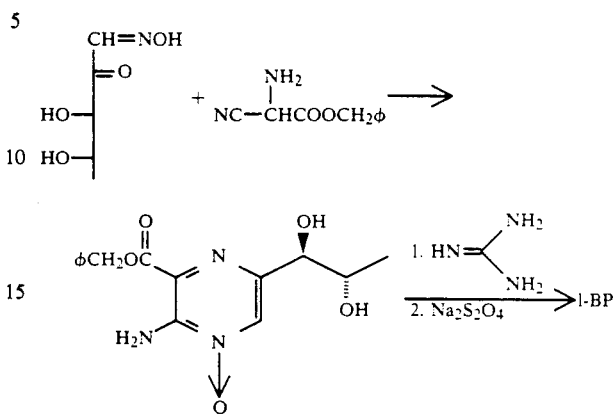

and condensation of the resulting 3-(1,2-dihydroxypropyl)-pyrazine-1-oxide derivatives with guanidine followed by deoxygenation of the N-oxide (E. C. Taylor et al., J. Am. Chem. Soc., 96, 6781 (1974)), (5) Reaction of α-hydroxyketone (prepared from crotonic acid) and TAP in accordance with the following reaction formula

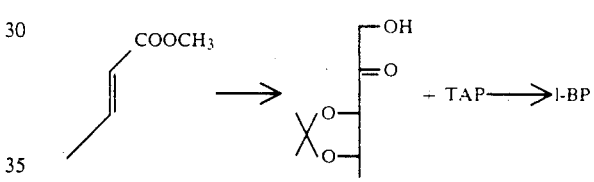

(M. Viscontini et al., Helv. Chim. Acta., 55, 574 (1972)) and (6) Reaction of TAP having protected hydroxyl group and 4-acetoxy-2,3-epoxypentanal in accordance with the following reaction formula

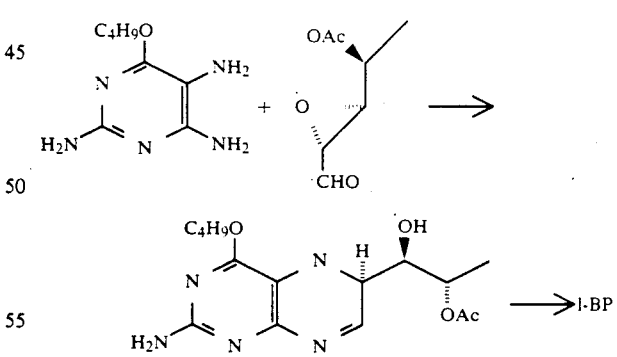

followed by oxidation with iodine and deprotection (Matsuura et al., Chemistry of Organic Synthesis, Vol. 46, No. 6, p. 570 (1988)).

The prior processes (1) to (4) starting from 5-deoxy-L-arabinose are not economically advantageous, since 5-deoxy-L-arabinose is difficult to be available industrially in large quantities and it is prepared starting from expensive L-rhamnose followed by subjecting to known degradation in sugar chemistry.

The prior processes (5) and (6) are not started from L-rhamnose but have the disadvantages in that biopterin is produced in a dl-form and optical resolution is required for obtaining the desired l-biopterin, thus leading to complicated process step and low yield.

Thus there has been demanded a process for the preparation of l-biopterin in good yield using inexpensive starting material.

In view of the above matters, we have proposed a process for the preparation of l-biopterin starting from (S)-alkyl lactate as disclosed in Japanese Kokai No. 221380/1989. That process comprises protecting the hydroxyl group of S-alkyl lactate with a trityl group, reducing a resulting alkyl 2-trityloxypropionate to (S)-2-trityloxypropanol, oxidizing it to (S)-2-trityloxy-propanal, treating it with a 2-furyl metal compound to form (1S, 2S)-1-(2-furyl)-2-trityloxy-1-propanal followed by oxidation and hydrolysis to form 2,3-dideoxy-6-trityloxyhepto-2-enopyranose-4-ulose, reducing it to 6-trityloxyhepto-2-ene-1,4,5-triol, acylating it to from 1,4,5-triacyloxy-6-trityloxyhepto-2-ene followed by oxidation to afford 2,3 diacyloxy-4-hydroxy-1-pentanal, treating it with phenylhydrazine to from a hydrazine, and condensing the hydrazine with a 3,5,6-triaminopyrimidinol followed by oxidation and deacylation.

DISCLOSURE OF THE INVENTION

Our further study has achieved new processes for the preparation of l-biopterin which include starting from D-ribose, synthesizing 5-deoxy-L-ribose via several intermediates and reacting 5-deoxy-L-ribose phenylhydrazone or its acylated compounds with an acid addition salt of 4-hydroxy-2,5,6-triaminopyrimidine. Thus the present invention provides alternative sources and processes of preparing l-biopterin.

On one hand, the intermediate of the present invention, 5-deoxy-2,3-O-cyclohexylidene-L-ribose has been synthesized by Lett et al. via several steps from myoinositol (Bull. Soc. Chim. Fr., 2299 (1972)). 5-Deoxy-L-ribose has been synthesized by Snyder et al. via several steps from rhamnose (Carbohydrate Res., 163, 169 (1987)). These processes have the disadvantage that a large number of isomers may be by-produced in the course of the reaction.

Thus there is also a need for alternative methods of obtaining 5-deoxy-L-ribose in good yield by high selective reaction using more inexpensive starting materials.

SUMMARY OF THE INVENTION

This invention relates to the processes of preparing l-biopterin which comprise the steps of:

Subjecting to selective Grignard reaction D-ribose having the hydroxyl groups in the 2- and 3-positions protected by an acetal group to give 6-deoxy-3,4-O-alkylidene allitol;

subjecting the 1- and 2-positions of said allitol to oxidative cleavage to form 5-deoxy-2,3-O-alkylidene-L-ribose followed by deacetalization to give 5-deoxy-L-ribose;

reacting 5-deoxy-L-ribose with a hydrazine compound to form a 5-deoxy-L-ribose hydrazone compound; and subjecting said hydrazone compound to condensation reaction with an acid addition salt of 4-hydroxy-2,5,6-triaminopyrimidine followed by oxidation.

The processes of the invention further comprise acylating the 5-deoxy-L-ribose hydrazone compound, subjecting the acylated hydrazone compound to condensation reaction with an acid addition salt of 4-hydroxy-2,5,6-triaminopyrimidine followed by oxidation and deacylation.

DETAILED DESCRIPTION OF THE INVENTION

The compounds of this invention can be prepared starting from D-ribose which is more inexpensive than the starting compounds used in the prior processes. The preferred embodiments of the present invention are illustrated using the reaction scheme which may be shown schematically below.

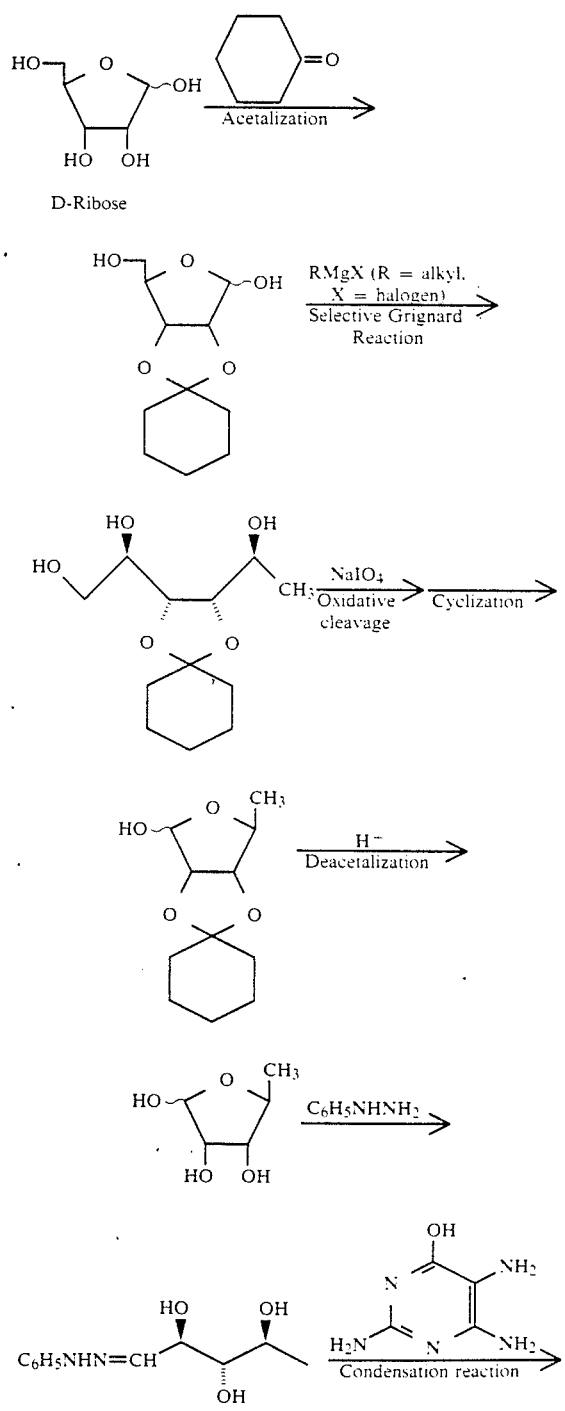

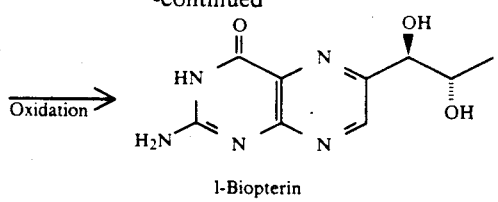

l-Biopterin

D-ribose is protected in the hydroxyl groups at the 2- and 3-positions with an acetal group by reaction with a ketone compound (e.g. cyclohexanone) or its acetal form in the presence of a catalytic amount of an acid (e.g. p-toluene sulfonic acid), thereby forming 2,3-O-alkylidene-D-ribose (e.g. 2,3-O-cyclohexylidene-D-ribose). This reaction is carried out using equimolecular or excess amounts of the ketone or its acetal form and D-ribose, usually excess amounts of them. The ketone compounds or the acetal forms thereof used in the reaction include acetone, diethyl ketone, methyl ethyl ketone, cyclopentanone, cyclohexanone, 2,2-dimethoxypropane, 1,1-dimethoxycyclohexanone and the like. The reaction may be conducted in the presence of an inert solvent (e.g. dimethyl formamide). The acid catalysts such as an organic acid (e.g. p-toluene sulfonic acid) are used in an amount of 0.01 to 0.1 mole, usually 0.02 mole based on D-ribose. The temperature of the reaction can be in the range between room temperature and the boiling point of the ketone compounds or the acetal forms thereof. This reaction results in D-ribose wherein the hydroxyl groups in the 2- and 3-positions are protected with the acetal group, i.e., 2,3-O-alkylidene-D-ribose.

The 2,3-O-alkylidene-D-ribose is subjected to selective Grignard reaction by which a chain is extended in the hemiacetal moiety. The Grignard reagents used in this reaction include alkylmagnesium halides such as methylmagnesium iodide, methylmagnesium bromide, methylmagnesium chloride. This reaction is accomplished using 3 to 20 moles, usually 10 moles of Grignard reagents per mole of 2,3-O-alkylidene-D-ribose. In this case an inert solvent may be used which includes ether, dimethoxymethane, tetrahydrofuran or the like. The temperature of the reaction can be in the range between $-20°$ C. and room temperature. The time of the reaction can be in the range of 2 to 24 hours, usually 4 to 12 hours. This reaction produces 6-deoxy-3,4-O-alkylidene allitol, e.g. 6-deoxy-3,4-O-cyclohexylidene-L-allitol which is a new compound which has not yet been disclosed in any literature.

The resulting allitol is subjected to oxidative cleavage by which the 1,2-diol moiety is converted into the aldehyde group. In the reaction metaperiodate is used as an oxidizing agent. For example sodium metaperiodate is used in an amount of 1.0 to 1.5 mole, usually 1.3 mole per mole of the allitol. The reaction is carried out usually in an inert organic solvent, e.g. two layer system consisting of ether of benzene and water. The reaction temperature can be in the range between 0° C. and the boiling point of the solvent. An alternative method of oxidation includes any oxidation reaction for the cleavage of the 1,2-diol moiety, an example of which is the reaction using as an oxidizing agent chromic acid, lead tetraacetate, iodosyl compounds or oxygen and the like. The oxidative cleavage reaction results in 5-deoxy-2,3-O-alkylidene-L-ribose, e.g. 5-deoxy-2,3-O-cyclohexylidene-L-ribose wherein the hydroxyl groups in the 2- and 3- positions are protected with cyclohexylidene acetal.

The resulting 5-deoxy-2,3-O-alkylidene-L-ribose is deacetalized by hydrolysis to form 5-deoxy-L-ribose. This reaction is carried out under usual conditions for deacetalization. For example the reaction can be performed in a mixed solvent comprising 1% $H_2SO_4$, 0.1N HCl or 0.2N HCl aqueous solution or water and an inert solvent such as THF, 1,4-dioxane, isopropyl alcohol, dimethoxy ethane, diglyme in the range between 0° C. and the boiling point of the solvent. In this case the reaction may be carried out in the presence of an acid catalyst such as a strong acid ion-exchange resin (e.g. DOWEX 50 W, Amberlite IR-120B, 118, etc.).

The resulting 5-deoxy-L-ribose, after reaction with a hydrazine compound is subjected to condensation reaction with an acid addition salt of 4-hydroxy-2,5,6-triaminopyrimidine followed by oxidation reaction. The hydrazine compounds which can be used include phenylhydrazines which may be substituted with $C_1-C_3$ alkyl (substituted or unsubstituted), $C_1-C_3$ alkoxy, halogen, nitro, substituted amino or acyloxy, e.g. phenylhydrazine, o-tolylhydrazine, m-tolylhydrazine, p-tolylhydrazine, 4-methoxyphenylhydrazine, 2-chlorophenylhydrazine, 3-chlorophenylhydrazine and 4-chlorophenylhydrazine, phenylhydrazine being preferable. For example 5-deoxy-L-ribose is reacted with phenylhydrazine in an alcohol (e.g. methanol) to form 5-deoxy-L-ribose phenylhydrazone. This phenylhydrazone is a new compound which has not yet been disclosed in any literature. Then the hydrazone is reacted with e.g. 4-hydroxy-2,5,6-triaminopyrimidine.2HCl in a suitable solvent, e.g. a mixed solution of water and methanol in the presence of 2-mercaptoalcohol (e.g., 2-mercaptoethanol) to form a condensate. The reaction is carried out at a temperature between room temperature and 70° C. for 1-2 hrs. Subsequently the condensate is oxidized for example by addition of an aqueous formic acid solution of iodine, potassium iodide and potassium ferricyanide to give a desired product, l-biopterin.

Alternatively, the phenylhydrazone may be acylated with a suitable acylating agent (e.g. anhydrous acetic acid) and the acylate is reacted with e.g. 4-hydroxy-2,5,6-triaminopyrimidine.$H_2SO_4$ in a suitable solvent (e.g. a mixed solution of water and methanol) in the presence of e.g. potassium acetate and sodium hydrosulfite. This reaction is carried out at a temperature between room temperature and 70° C. for 12-48 hrs. Subsequently the reaction product is oxidized for example by addition of a methanol solution of iodine followed by deacetylation with e.g. ammonia water under acidic condition or with e.g. dilute hydrochloric acid solution or dilute acetic acid solution under acidic condition whereby there can be prepared desired l-biopterin.

The invention is further illustrated by the following non-limitative examples.

EXAMPLE 1

D-ribose (30.0 g, 0.200 mol) was suspended in cyclohexanone (200 ml), p-toluene sulfonic acid (0.70 g, 3.68 mmol) was added and the mixture was reacted overnight at room temperature. The reaction solution was extracted with ethyl acetate (2×500 ml), washed in sequence with water (300 ml), saturated sodium bicarbonate solution (300 ml) and saturated brine solution (300 ml). The solution was dried over anhydrous magnesium sulfate and then concentrated in vacuo to afford 55 g of a pale yellow oil. Purification of this crude product by silica gel column chromatography (SiO$_2$, 300 g, CHCl$_3$—CHCl$_3$/CH$_3$OH=20/1) gave 43.6 g of 2,3-O-cyclohexylidene-D-ribose as a light yellow oil (yield 95%).

n$_D^{23}$1.4938, [α]$_D^{26}$−20.8°(c=1.01, CHCl$_3$), IR $\nu_{max}$(-film)cm$^{-1}$: 3400(s), 2940(s), 2865 (m), 1455(m), 1375(m), 1338(w), 1290(w), 1252 (w), 1235(m), 1168(m), 1104(s), 1160(m), 1000 (w), 945(m), $^1$H-NMR δ: 1.45–1.85(m, 10H), 3.72 (d, 2H, J=2 Hz), 4.40(s, 1H), 4.57(d, 1H, J=6 Hz), 4.81 (d, 1H, J=6 Hz), 5.42 (s, 1H).

|  | C | H |
|---|---|---|
| Found: | 57.39 | 7.93 |
| C$_{11}$H$_{18}$O$_5$ (230.3) Calcd.: | 57.38 | 7.88 |

EXAMPLE 2

Ether (210 ml) and iodine crystal (small amount) were added to metallic magnesium (52.8 g, 2.17 mol) and to the mixture were carefully added dropwise about 100 ml of an ether solution (100 ml) of methyl iodide (324 g, 2.28 mol). After the reaction started, the remaining methyl iodide solution was added dropwise while slowly stirring at such rate as to maintain a mild reflux. After completion of the addition, a water bath was removed and the mixture was stirred at room temperature for 45 minutes.

The resultant methyl magnesium iodide solution was cooled to −10° C. on a salt/ice bath and a THF solution (400 ml) of 2,3-O-cyclohexylidene-D-ribose (50.0 g, 0.217 mol) was added dropwise over a period of 1 hour while keeping an internal temperature below 5° C. After completion of the addition, the ice bath was removed and the mixture was stirred at room temperature for 5 hours and then left to stand overnight.

The reaction solution was cooled on a salt/ice bath and an aqueous saturated ammonium chloride solution (500 ml) was added dropwise. To the resulting solid material was added water (400 ml) and the mixture was stirred at room temperature for 1 hour. A grayish white slurry reaction solution was extracted with ethyl acetate (500 ml). The aqueous layer was further extracted three times with ethyl acetate (500 ml), the combined organic layer was washed with water and saturated brine solution, dried over anhydrous magnesium sulfate and concentrated in vacuo. The resultant orange crude product (50.8 g) was purified by silica gel column chromatography (SiO$_2$: 350 g, CHCl$_3$) to afford 48.7 g of 6-deoxy-3,4-O-cyclohexylidene-L-allitol as a pale yellow oil (yield 91%).

n$_D^{23}$ 1.4870, [α]$_D^{26}$=20.9°(c=1.20,CHCl$_3$), IR $\nu_{max}$(-film)cm$^{-1}$: 3350(s), 2940(s), 1455(m), 1372(m), 1338(w), 1280(m), 1235(w), 1170(m),1100(s), 1045(s), 942(m), 905(m), $^1$H-NMR δ: 1.34(d, 3H, J=6 Hz), 1.30–1.45(bs, 2H), 1.45–1.70(s, 8H), 3.60(b, 3H), 3.65–4.15(m, 6H).

|  | C | H |
|---|---|---|
| Found: | 58.53 | 9.04 |
| C$_{12}$H$_{22}$O$_5$ (246.3) Calcd.: | 58.52 | 9.00 |

Alternatively, 6-deoxy-3,4-O-cyclohexylidene-L-allitol was prepared by the following procedure.

THF (38 ml) and iodine crystal (small amount) were added to magnesium turnings (1.83 g, 75.3 mmol) and methyl chloride gas was blown into the mixture at room temperature while vigorously stirring. After the reaction started, the mixture was cooled on a water bath in such a manner that THF maintained slow reflux. After the magnesium turnings reacted completely, blowing of methyl chloride gas was discontinued and the mixture was stirred at room temperature for 30 minutes. The resultant methyl magnesium chloride solution was cooled to −10° C. on a salt/ice bath and a THF solution (20 ml) of 2,3-O-cyclohexylidene-D-ribose (1.73 g, 75.1 mmol) was added dropwise over a period of 30 minutes while keeping the internal temperature below 5° C. After completion of the addition, the ice bath was removed and the mixture was stirred at room temperature for 5 hours, then the reaction solution was cooled on a salt/ice bath and an aqueous saturated ammonium chloride solution (20 ml) was added dropwise while slowly stirring. To the resulting solid material was added water (20 ml), the mixture was stirred at room temperature for 1 hour and a grayish white slurry reaction solution was extracted with ethyl acetate (40 ml). The aqueous layer was further extracted with ethyl acetate (40 ml), the combined organic layer was washed with water and saturated brine solution, dried over anhydrous magnesium sulfate and concentrated in vacuo. The resulting colorless crude product (1.70 g) was purified by silica gel column chromatography (SiO$_2$: 40 g, CHCl$_3$) to provide 1.51 g of 6-deoxy-3,4-O-cyclohexylidene-L-allitol as a colorless oil (yield 82%).

EXAMPLE 3

Into a solution of the triol (46.0 g, 0.187 mol) in ether (700 ml) was poured slowly under ice-cooling a solution of sodium metaperiodate (54.0 g, 0.253 mol) in water (400 ml), the mixture was stirred for 1 hour, the organic layer was separated and the aqueous layer was extracted twice with ethyl acetate (800 ml). The combined organic layer was washed with saturated sodium bicarbonate solution and saturated brine solution, dried over anhydrous magnesium sulfate and concentrated to afford 33.9 g of a pale yellow oil. The oil was purified by silica gel column chromatography (SiO$_2$: 300 g, CHCl$_3$) to give 30.5 g of 5-deoxy-2,3-O-cyclohexylidene-L-ribose as a light yellow oil (yield 76%).

n$_D^{23}$ 1.4818, [α]$_D^{26}$+36.1°(c=1.19,CHCl$_3$), IR $\nu_{max}$(-film)cm$^{-1}$: 3430(s), 2940(s), 2865 (m), 1455(m), 1375(m), 1338(w), 1285(w), 1232(w), 1168(m), 1105(s), 1062(s), 995(m), 944(m), $^1$H-NMR δ: 1.34(d, 3H, J=7 Hz), 1.30–1.50(m, 2H), 1.55–1.85(m, 8), 3.51 (d, 1H, J=2 Hz), 4.36(q, 1H, J=6 Hz), 4.55 (d, 1H, J=6 Hz), 4.66(d, 1H, J=6 Hz), 5.44 (d, 1H, J=2 Hz).

|  | C | H |
|---|---|---|
| Found: | 61.54 | 8.48 |
| C$_{11}$H$_{18}$O$_4$ (214.3) Calcd.: | 61.66 | 8.47 |

EXAMPLE 4

0.2 N HCl solution (150 ml) was added to a solution of 5-deoxy-2,3-O-cyclohexylidene-L-ribose (27.3 g, 0.128 mol) in 1,4-dioxane (150 ml), the mixture was reacted at a bath temperature of 60° C. for 3 hours and further at 70° C. for 7 hours and the reaction solution was cooled and adjusted to pH 7 with diluted ammonia water. The reaction solution was concentrated in vacuo to ⅓ of the total amount, the remaining solution was washed twice with chloroform (200 ml) and the solution was concentrated to give 14.7 g of a yellow oil. The chloroform layer was concentrated to recover unreacted starting material as 5.00 g of a yellow oil. A part of the resulting crude 5-deoxy-L-ribose was reacted with phenylhydrazine in methanol to form the hydrazone for analysis, the remainder being used for the starting material for the subsequent reaction.

The analysis of the product as phenylhydrazone is shown below.

Analysis for 5-deoxy-L-ribose phenylhydrazone:
m.p. 115°–117° C.,

IR $\nu$max (KBr)cm$^{-1}$: 3450(s), 3270(s), 3200(s), 2940(m), 1610(s), 1532(m), 1500(m), 1452(m), 1432(w), 1410(w), 1340(w), 1250(w), 1260(s), 1140(m), 1125(m), 1062(s), 1010(s), 928(w), 888(m).

EXAMPLE 5

The crude 5-deoxy-L-ribose (14.7 g) prepared in Example 4 was dissolved in methanol (150 ml), phenylhydrazine (12.0 g, 0.111 mol) and acetic acid (0.1 ml) were added, the mixture was left to stand at room temperature for 2 hours and the reaction solution was concentrated in vacuo. The residue was washed with isopropyl ether and hexane and the resulting crude phenylhydrazone (about 18.9 g) was subjected to the subsequent reaction.

4-Hydroxy-2,5,6-triaminopyrimidine 2HCl (18.0 g, 0.084 mol) was suspended in a mixed solution (540 ml) of methanol and water (3:2), to which was added dropwise mercaptoethyl alcohol (1.0 ml) and then a solution of the crude phenylhydrazone (18.9 g) as previously prepared in a mixed solution (200 ml) of methanol and water (3:2) was poured into the suspension. The mixture was stirred in an argon atmosphere at room temperature for 1 hour and then stirred under heat at 60°–70° C. for 40 minutes. The reaction solution was cooled to $-10°$ C. and into the solution was poured over a period of 10 minutes a solution of iodine (40 g, 0.158 mol), potassium iodide (66 g, 0.398 mol), potassium ferricyanide (40 g, 0.122 mol) and 80% formic acid (40 ml) in water (1 lit.). After air was bubbled into the solution at 0° C. for 1.5 hours, the reaction solution as concentrated in vacuo, the residue was extracted with 10% ammonia water (1 lit.), insoluble matter was filtered off, the filtrate was concentrated, the residue was again dissolved in 2% ammonia water (2 lit.) and separated by ion-exchange resin column chromatography (DOWEX 1×8; 10 cm×40 cm; 0.15 N ammonium formate buffer solution (pH 9)). The effluent was concentrated in vacuo, the residue was dissolved in 10% ammonia water (240 ml) and decolorized by activated charcoal. The solution was concentrated in vacuo to ⅓ of the total amount, left to stand overnight under ice-cooling, the precipitated pale yellow solid was washed with ice water and ethanol and dried in vacuo (80° C., 6 hrs.) to give 5.00 g (0.021 mole) of l-biopterin.

m.p. >300° C. (partially decomposed at ca. 270° C.), $[\alpha]_D^{24}$ −65.0° (c=0.2, 0.1N Hcl), IR$\nu$ $_{max}$(KBr)cm$^{-1}$: 3400(s), 3270(s), 2800(w), 1720(m), 1680(s), 1535(m), 1412(w), 1290(w), 1125(w), $^1$H-NMR $\delta$: 1.17 (d, 3H, J=6 Hz), 422 (q, 1H, J=6 Hz), 4.94 (d, 1H, J=5 Hz), 8.96 (s, 1H).

|  | C | H | N |
|---|---|---|---|
| Found: | 43.62 | 4.83 | 28.45 |
| $C_9H_{11}N_5O_3.\frac{1}{2}H_2O$ Calcd.: | 43.90 | 4.91 | 28.44 |

EXAMPLE 6

The phenylhydrazone (28.5 g, 0.127 mol) as obtained in the former part of Example 5 was dissolved in pyridine (200 ml) to which anhydrous acetic acid (100 ml) was added, the solution was left to stand at room temperature for 2 hours and the reaction solution was diluted with toluene (200 ml) and concentrated in vacuo. To the residue was added toluene (200 ml) and concentrated in vacuo. The resulting triacetyl form was dissolved in a mixed solution of methanol (400 ml) and pyridine (90 ml) and then into the solution were poured in sequence a solution of sodium hydrosulfite (3.0 g, 0.017 mol) and sodium acetate. 3 hydrate (38.5 g, 0.283 mole) in water (900 ml) and a suspension of 4-hydroxy-2,5,6-triaminopyrimidine. $H_2SO_4$ (30.0 g, 0.125 mol) in water (1200 ml). The resulting solution was purged with argon and reacted at a bath temperature of 40°–45° C. for 24 hours. To the resulting reddish brown solution was added dropwise over a period of about 50 minutes a solution of iodine (75.0 g, 0.926 mol) in methanol (900 ml). The reaction solution was concentrated to about 300 ml, a reddish brown suspended solution was cooled on a salt/ice bath for 1 hour and the precipitate was collected by filtration. This precipitate was washed with cold water (160 ml), cold ethanol (300 ml) and ether (300 ml) to afford crude diacetyl biopterin. This crude product was dissolved in hot water (3.5 lit.), decolorized by activated charcoal, cooled on a salt/ice bath for 2 hours, the precipitated pale yellow solid was collected by filtration, washed with cold water (50 ml), cold ethanol (50 ml) and ether (50 ml) and dried to give 12.9 g (0.040 mole) of diacetyl biopterin. This diacetyl product was dissolved in 3N HCl (130 ml), reacted under heat at 50°–60° C. for 3 hours, the reaction solution was concentrated in vacuo and the residual red syrup extracted with diluted ammonia water (200 ml). The extracted solution was concentrated in vacuo to 50 ml of the remaining amount and the concentrated solution was left to stand overnight in a refrigerator. The precipitated pale yellow solid was collected by filtration, washed with cold water (20 ml), cold ethanol (20 ml) and ether (20 ml) and dried. The resulting solid was recrystallized from 20% aqueous acetic acid solution to afford 9.90 g (0.042 mol) of l-biopterin.

What is claimed is:

1. A process of preparing l-biopterin which comprises the steps of:
   reacting D-ribose with a ketone compound or its acetal form to afford a 2,3-0-alkylidene-D-ribose having the hydroxyl groups at the 2- and 3-positions protected by an acetal group;
   reacting the 2,3-O-alkylidene-D-ribose with an methylmagnesium halide to obtain a 6-deoxy-3,4-O-alkylidene allitol;
   treating the 6-deoxy-3, 4-O-alkylidene allitol with a metaperiodate, chromic acid, lead tetraacetate, an iodosyl compound or oxygen to form a 5-deoxy-2, 3-O-alkylidene-L-ribose followed by deacetalization to give 5-deoxy-L-ribose;
   reacting 5-deoxy-L-ribose with an arylhydrazine to form a 5-deoxy-L-ribose arylhydrazone; and condensing the arylhydrazone with 4-hydroxy-2, 5, 6-triaminopyrimidine and its salts followed by oxidation with iodine or its mixture, hydrogen peroxide, oxygen or a combination thereof.

2. A process of claim 1 wherein the 6-deoxy-3,4-O-alkylidene allitol is 6-deoxy-3, 4-O-cyclohexylidene-L-allitol.

3. A process of claim 1 wherein the 5-deoxy-L-ribose arylhydrazone is 5-deoxy-L-ribose phenylhydrazone.

4. A process of preparing l-biopterin which comprises the steps of:

reacting D-ribose with a ketone compound or its acetal form to afford a 2,3-O-alkylidene-D-ribose having the hydroxyl groups at the 2- and 3-positions protected by an acetal group;

reacting the 2,3-O-alkylidene-D-ribose with an methylmagnesium halide to obtain a 6-deoxy-3,4-O-alkylidene allitol;

treating the 6-deoxy-3, 4-O-alkylidene allitol with a metaperiodate, chromic acid, lead tetraacetate, an iodosyl compound or oxygen to form a 5-deoxy-2, 3-O-alkylidene-L-ribose followed by deacetalization to give 5-deoxy-L-ribose;

reacting 5-deoxy-L-ribose with an arylhydrazine to form a 5-deoxy-L-ribose arylhydrazone;

condensing the arylhydrazone with 4-hydroxy-2, 5, 6-triaminopyrimidine and its salts followed by oxidation with iodine or its mixture, hydrogen peroxide, oxygen or a combination thereof to form diacetyl biopterin; and subjecting diacetyl biopterin to deacetylation.

5. A process of claim 4 wherein the 6-deoxy-3,4-O-alkylidene allitol is 6-deoxy-3,4-O-cyclohexylidene-L-allitol.

6. A process of claim 4 wherein the 5-deoxy-L-ribose arylhydrazone is 5-deoxy-L-ribose phenylhydrazone.

* * * * *